(12) United States Patent
Tai et al.

(10) Patent No.: US 9,211,234 B2
(45) Date of Patent: Dec. 15, 2015

(54) CONFIGURABLE PERCUTANEOUS ENDOSCOPIC GASTROSTOMY TUBE

(75) Inventors: Kok-Ming Tai, Lawrenceville, GA (US); Alison S. Bagwell, Alpharetta, GA (US); Andrew T. Baker, Norcross, GA (US); Emily A. Reichart, Atlanta, GA (US); Phillip A. Schorr, Cumming, GA (US)

(73) Assignee: AVENT, INC., Alpharetta, GA (US)

( * ) Notice: Subject to any disclaimer, the term of this patent is extended or adjusted under 35 U.S.C. 154(b) by 1048 days.

(21) Appl. No.: 13/245,542

(22) Filed: Sep. 26, 2011

(65) Prior Publication Data

US 2012/0078174 A1 Mar. 29, 2012

Related U.S. Application Data

(60) Provisional application No. 61/386,793, filed on Sep. 27, 2010, provisional application No. 61/446,229, filed on Feb. 24, 2011.

(51) Int. Cl.
*A61M 29/00* (2006.01)
*A61J 15/00* (2006.01)
*A61B 17/34* (2006.01)
*A61M 25/10* (2013.01)
*A61M 29/02* (2006.01)

(52) U.S. Cl.
CPC ......... *A61J 15/0015* (2013.01); *A61B 17/3415* (2013.01); *A61J 15/0038* (2013.01); *A61J 15/0042* (2013.01); *A61M 25/1002* (2013.01); *A61M 29/02* (2013.01)

(58) Field of Classification Search
CPC .............. A61J 15/0015; A61J 15/0038; A61J 15/0026; A61J 15/0034; A61J 15/00342; A61J 15/003; A61M 2025/0233; A61M 2039/0297

See application file for complete search history.

(56) References Cited

U.S. PATENT DOCUMENTS

| | | |
|---|---|---|
| 3,397,699 A | 8/1968 | Kohl |
| 3,633,579 A | 1/1972 | Alley et al. |
| 4,315,513 A | 2/1982 | Nawash et al. |
| 4,393,873 A | 7/1983 | Nawash et al. |
| 4,531,943 A | 7/1985 | Van Tassel et al. |
| 4,627,838 A | 12/1986 | Cross et al. |
| 4,758,219 A | 7/1988 | Sacks et al. |
| 4,850,953 A | 7/1989 | Haber et al. |
| 4,861,334 A | 8/1989 | Nawaz |

(Continued)

FOREIGN PATENT DOCUMENTS

| | | |
|---|---|---|
| EP | 0 824 929 B1 | 10/2003 |
| EP | 1674125 B1 * | 4/2009 |

(Continued)

*Primary Examiner* — Emily Schmidt
(74) *Attorney, Agent, or Firm* — Dority & Manning, PA (57) ABSTRACT

A configurable percutaneous endoscopic gastrostomy tube includes a shaft having a distal end and a proximal end. The shaft defines a lumen therethrough for passage of a feeding solution or medicine. An expandable retainer is located on the shaft, the retainer having a deployed position and an insertion position. The tube includes a releasable lock for maintaining the expandable retainer in its deployed position, the releasable lock located on the shaft proximal to the expandable retainer. A flexible sheath surrounds the expandable retainer, the sheath being generally loose around the retainer when the retainer is in an insertion position and the sheath being generally snug against an exterior surface of the retainer when the retainer is in a deployed position.

14 Claims, 9 Drawing Sheets

(56) References Cited

U.S. PATENT DOCUMENTS

| | | |
|---|---|---|
| 5,073,166 A | 12/1991 | Parks et al. |
| 5,248,302 A | 9/1993 | Patrick et al. |
| 5,336,203 A | 8/1994 | Goldhardt et al. |
| 5,356,391 A | 10/1994 | Stewart |
| 5,374,254 A | 12/1994 | Buma |
| 5,429,598 A | 7/1995 | Waxman et al. |
| 5,702,365 A * | 12/1997 | King ............... 604/105 |
| 6,030,361 A | 2/2000 | Miyashiro |
| 6,030,406 A | 2/2000 | Davis et al. |
| 6,039,714 A | 3/2000 | Cracauer et al. |
| 6,077,250 A | 6/2000 | Snow et al. |
| 6,186,985 B1 | 2/2001 | Snow |
| 6,322,538 B1 | 11/2001 | Elbert et al. |
| 6,364,858 B1 | 4/2002 | Picha |
| 6,881,420 B2 | 4/2005 | Flashner-Barak et al. |
| 6,896,665 B2 | 5/2005 | Picha et al. |
| 6,918,888 B2 | 7/2005 | Gershowitz |
| 6,942,641 B2 | 9/2005 | Seddon |
| 7,083,595 B2 | 8/2006 | Chu et al. |
| 7,232,426 B2 | 6/2007 | Itrich et al. |
| 7,547,303 B2 | 6/2009 | DeLegge |
| 7,654,980 B2 | 2/2010 | Weststrate et al. |
| 7,771,396 B2 | 8/2010 | Stefanchik et al. |
| 2003/0225392 A1 | 12/2003 | McMichael et al. |
| 2004/0049157 A1 | 3/2004 | Plishka et al. |
| 2005/0085771 A1 * | 4/2005 | Lyon ............... 604/107 |
| 2006/0030818 A1 | 2/2006 | McVey |
| 2006/0270989 A1 | 11/2006 | McMichael et al. |
| 2007/0078465 A1 | 4/2007 | Williams et al. |
| 2007/0233005 A1 * | 10/2007 | McMichael et al. ..... 604/164.01 |
| 2007/0239171 A1 | 10/2007 | Stefanchik et al. |
| 2007/0255222 A1 | 11/2007 | Li et al. |
| 2009/0024091 A1 | 1/2009 | Li et al. |
| 2009/0318854 A1 | 12/2009 | Bailey |
| 2009/0318873 A1 | 12/2009 | Bailey |
| 2010/0022969 A1 | 1/2010 | Renaux |
| 2011/0137252 A1 | 6/2011 | Oster et al. |

FOREIGN PATENT DOCUMENTS

| | | | |
|---|---|---|---|
| GB | 2 428 198 A | 1/2007 | |
| GB | 2428198 A * | 1/2007 | |
| WO | WO 99/02093 A1 | 1/1999 | |
| WO | WO 03/092708 A2 | 11/2003 | |
| WO | WO 03/092780 A2 | 11/2003 | |
| WO | WO 2004/112877 A1 | 12/2004 | |
| WO | WO 2004112879 A1 * | 12/2004 | ............ A61M 25/04 |
| WO | WO 2010/075032 A2 | 7/2010 | |
| WO | WO 2011/053242 A1 | 5/2011 | |

* cited by examiner

CONFIGURABLE PERCUTANEOUS ENDOSCOPIC GASTROSTOMY TUBE

This application claims the benefit of priority from U.S. Provisional Application No. 61/386,793 filed on Sep. 27, 2010 and U.S. Provisional Application No. 61/446,229 filed on Feb. 25, 2011, the contents of which are incorporated herein by reference.

FIELD OF THE INVENTION

The present invention relates to catheters such as feeding tubes and their placement in the body of a patient.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is commonly referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. These percutaneous transconduit catheters (sometimes referred to as "percutaneous transconduit tubes") are frequently referred to as "gastrostomy catheters", "percutaneous gastrostomy catheters", "PEG catheters" or "enteral feeding catheters". U.S. Pat. No. 6,019,746 for a "Low Profile Balloon Feeding Device" issued to Picha et al. on Feb. 1, 2000, provides an example of one device.

A problem universal to low profile and non-low profile enteral feeding devices or enteral feeding assemblies (e.g., gastrostomy tubes) is the difficulty in inserting a retainer in a body lumen to hold the enteral feeding assembly in a fixed position in the lumen. Balloons have been used, which are deflated for insertion through the stoma and then inflated to hold the enteral feeding assembly in position. While balloons have many advantages, balloon may eventually leak and deflate. Other retaining fixtures have been difficult to insert through a stoma, and often must be endoscopically placed by a physician, usually during a surgical procedure. These retaining fixtures are typically made of the same silicone composition used to make the enteral feeding device and are frequently molded as part of the device. The end which is inserted into a body lumen may have a Malecot tip consisting of three or four generally semicircular loops of material which radiate from the end of the tube and join at a tip. The radial loop sections can seat against the interior stomach wall so as to impede the inadvertent withdrawal of the tube. Liquid nutrient passes from the tube into the stomach through the openings between these semicircular loops. Examples of conventional devices with Malecot tips or similar expanding tips are found at, for example, U.S. Pat. No. 3,915,171 for "Gastrostomy Tube" issued to Shermeta; U.S. Pat. No. 4,315,513 for "Gastrostomy and Other Percutaneous Transport Tubes" issued to Nawash et al.; U.S. Pat. No. 4,944,732 for "Gastrostomy Port" issued to Russo; and U.S. Pat. No. 5,484,420 for "Retention Bolsters for Percutaneous Catheters" issued to Russo. Exemplary commercial products include the Passport® Low Profile Gastrostomy Device available from Cook Medical, Inc. of Bloomington, Ind. and the Mini One™ Non-Balloon Button available from Applied Medical Technology, Inc. of Brecksville, Ohio.

Figure 1:
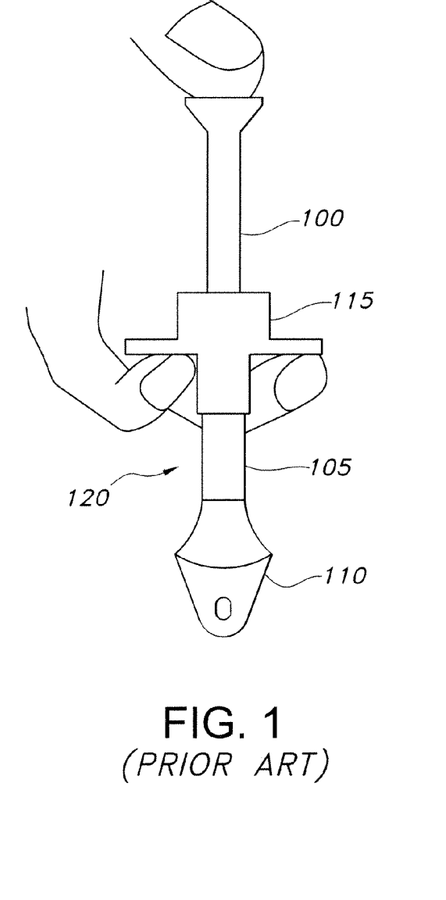
FIG. 1 is an illustration of a conventional prior art device in which a stylet is positioned in the device but force has not been applied to elongate the device.
Figure 2:
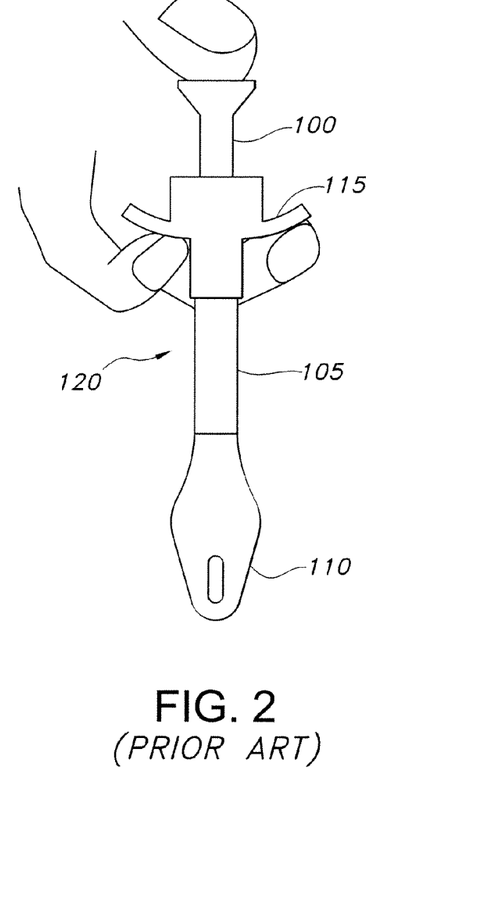
FIG. 2 is an illustration of a conventional prior art device in which a stylet is positioned in the device and force is applied to elongate the device.

A shortcoming of these devices relates to the manner of insertion and withdrawal of a catheter or tube incorporating these retaining fixtures (e.g., a gastrostomy tube) into a body lumen such as into the stomach. As generally illustrated in FIG. 1, this is typically accomplished by a surgeon who inserts a stylet 100 through the length of the tube 105 and up against the end of the Malecot tip or similar expanding tip 110 while gripping the device 115 at its base 120. Referring now to FIG. 2, as the surgeon pushes the stylet 100 and tube 105 through the abdominal wall opening, the force of the end of the stylet 100 elongates the entire device 120 from about the base 115 to the tube 105 and the Malecot tip or similar expanding tip 110, thereby stretching and/or pulling the semicircular sections into a straight, elongated configuration (or stretching and/or pulling the similar expanding tip into an elongated configuration). When so elongated, the Malecot tip (or similar expanding tip) can pass through a gastrostomy opening into the stomach. When the stylus then is withdrawn, the resiliency of the tube material pulls the elongated sections of the Malecot tip back into semicircular configuration (or allows the similar expanding tip to retract to its expanded configuration), thereby securing the end within the stomach.

In practice, both the tube and the Malecot tip or similar expanding tip stretch which require providing much greater length of the article being inserted through a gastrostomy opening. This elongation of both the tube and the Malecot tip or similar expanding tip also makes withdrawal of the device more difficult because the stylet must be inserted further into the body. This presents difficulties for smaller patients, particularly for children and babies. In addition, much greater force is required to extend both the tube and the Malecot tip or similar expanding tip. The greater travel of the stylet into the body in combination with greater force applied to the stylet creates more potential for harm if the stylet is not aligned properly on the Malecot tip or similar expanding tip, if the stylet slips off the tip or if the tip fails and separates from the tube.

Accordingly, there is a need for an enteral feeding assembly and associated insertion device(s) which permits a user or health care provider to quickly and easily insert the assembly, including the retainer, externally through the patient's stoma and into a body lumen, such as, for example, a stomach lumen. Such an assembly and retainer are desirably configured so that during insertion, the retainer has an outer diameter which is about the same as the outer diameter of the portion of the catheter which extends into the stoma. However, after insertion, it is desirable that the outer diameter of the retainer expands to hold the enteral feeding assembly in the desired position for enteral feeding. Moreover, it is desirable to have a retainer that may be expanded in a body lumen without inflation. Finally, it is desirable that any devices used to insert, expand, contract, and/or remove the retainer be simple and easy to use.

SUMMARY

In response to the difficulties and problems discussed herein, the present invention provides an innovative PEG device for placement in a gastric lumen, desirably under direct visualization using an endoscope. Since the stomach is a common example of a gastric lumen, for the purpose of describing the present invention, the use of the term "stomach" is representative of all other gastric lumens or spaces (e.g., duodenum, jejunum, ileum, etc.), unless otherwise specified.

According to the invention, the configurable PEG device (hereinafter referred to as a "C-PEG" or "C-PEG device") includes a shaft having a first or distal end that is in-dwelling and a second or proximal end that resides outside the body of a patient. The shaft defines a lumen for passage of feeding solutions and/or medicine. The shaft includes an expandable retainer secured to a portion of the shaft (e.g., a distal end of the shaft or between the distal end and a middle section or a mid-point of the shaft for various longer length devices), the retainer having a deployed position and an insertion position. The C-PEG also includes a flexible sheath surrounding the expandable retainer, the sheath being generally loose around the retainer when the retainer is in an insertion position and the sheath being generally snug against an exterior surface of the retainer when the retainer is in a deployed position.

The CPEG incorporates a releasable lock for maintaining the expandable retainer in its deployed position. The releasable lock is located on the shaft in a position proximal to the expandable retainer. For example, the releasable lock may be located at or near the second end of the shaft.

In an aspect of the present invention, the expandable retainer alternates between: (a) an insertion/removal state in which the expandable retainer has a first length such that flexible struts, ribs and/or other elements of the retainer are substantially axially aligned with the exterior of the shaft to give an effective cross-sectional area that is substantially the same as that of the shaft, and (b) a deployed state in which the retainer has a second length that is shorter than the first length in which the flexible struts, ribs and/or other elements of the retainer have a deployed effective cross-sectional area with a diameter that is substantially greater than that of the shaft.

The expandable retainer is generally in the form of a hollow sleeve or flexible skeleton that has two opposing ends. This sleeve is desirably formed of a flexible plastic mesh, braided mesh-like material, net or network of material, and/or flexible flat ribs composed of one or more materials such as, for example, PET (polyethylene terephthatlate), PEEK (poly (ether-ether-ketone)) or nylon (various polyamides). A substantial portion of the exterior surface of the retainer is covered in a flexible sheath that allows unencumbered changes in retainer shapes and states as desired. The flexible sheath avoids in-growth of tissue, is non-permeable to liquid, and is generally non-compliant (i.e., the flexible sheath is desirably not stretchable like an elastic material) although it may be somewhat compliant or even elastic—provided it remains a separate component and does not generate forces that deform the expandable retainer when deployed. This flexible sheath may be attached at or towards each opposing end of the retainer to envelop at least a substantial portion of the retainer but not to embed within it. The flexible sheath may snugly conform to the retainer in the deployed state. The sheath prevents liquid from passing from the exterior of the retainer through the retainer when the sheath and retainer are properly assembled as part of the C-PEG.

The shaft has at least a first tube and a second tube that are arranged to form at least one effective lumen that spans the entire length of the shaft (i.e., the entire length of the C-PEG). The first tube is desirably concentric within or surrounded by the second tube. That is, the first tube is generally an inner tube and the second tube is an outer tube. The first and second tubes are configured to axially slide with respect to each other. Generally speaking, the first tube is longer than the second tube. The first tube and the second tube have respective proximal and distal ends that correspond to the proximal and distal orientation of the shaft. In an aspect of the invention, the overall length of the C-PEG is not significantly altered when the retainer alternates between the insertion and deployed states.

Generally speaking, a first end or end portion of the retainer is joined to the distal portion or end of the first or inner tube and a second end or end portion of the retainer sleeve is joined to a distal portion or end of the second or outer tube. When the retainer is in an insertion position (or in an un-deployed state), the first or inner tube generally extends a distance beyond the end of the second or outer tube such that the first end of the retainer is extended axially and the rest of the retainer is pulled inwardly against the first and second tubes such that the retainer assumes a tubular configuration.

When the retainer is in a deployed position, it is configured to have a hemispherical-, dome- or mushroom-type shape. Such a shape is generated by retracting the first or inner tube back into the second or outer tube. This axial movement inverts the flexible (e.g. mesh) material of the retainer sleeve onto itself to create a resilient retention bumper. In an aspect of the invention, this axial movement inverts a portion of the mesh or braided material or other flexible material of the retainer sleeve onto itself to create a flatter proximal profile that provides greater stabilization than rounded or funneled profiles found in conventional retainers. In an aspect of the invention, the deployed retainer may define at least one generally planar surface and at least one generally frustoconical surface and/or cylindrical surface. For example, one or more generally planar surfaces may be generally perpendicular to the longitudinal axis of the shaft and one or more generally frustoconical surface and/or cylindrical surface may be generally parallel to the longitudinal axis of the shaft. In its deployed state, the mesh or braided material or other flexible material can be configured so that the fold-over edge of the mesh (i.e., the area where the mesh folds back or inverts on itself) can be drawn inwardly toward a center point or central axis of the shaft such that the problem of tissue growing over the top of the deployed retainer is reduced.

Another feature of the C-PEG is the ability for the distal end of the shaft to recess within the deployed retainer. That is, during deployment of the retainer, the distal end of the shaft is located in a more proximal position than the fold-over edge of the deployed retainer. This prevents the distal end of the shaft from contacting tissue when the retainer is in the deployed state.

According to the invention, a locking mechanism integrated with the C-PEG device locks the retainer in its deployed state. This may be accomplished by mechanical engagement, friction, compression or other techniques. One embodiment of a suitable locking mechanism is a spacer lock. When the first or inner tube is pulled or retracted into the second or outer tube towards the proximal end of the shaft to deploy the retainer, the proximal end of the first or inner tube will extend a predetermined distance beyond the proximal end of the second or outer tube. A spacer may be employed to prevent the second (i.e., outer) tube from returning to its initial insertion or un-deployed position.

In another locking embodiment, the locking mechanism does not utilize a spacer but instead uses a clamp to grip the tubing. After the retainer is deployed, the clamp is placed over the outside of the first tube and clamped to the tube with enough force to ensure the lock cannot move along the tube but not too much force as to deform the lumen of the device. The clamp may be placed on the first (i.e., inner) tube and clamped so that the second (i.e., outer) tube butts up against it and the clamp prevents the second outer tube from returning to its initial insertion state position.

A better understanding of the above and many other features and advantages of the configurable percutaneous endoscopic gastrostomy tube obtained from a consideration of the detailed description of the invention below, particularly if such consideration is made in conjunction with the appended drawings.

DETAILED DESCRIPTION

Reference will now be made in detail to one or more embodiments, examples of which are illustrated in the drawings. It should be understood that features illustrated or described as part of one embodiment may be used with another embodiment to yield still a further embodiment.

Figure 3A:
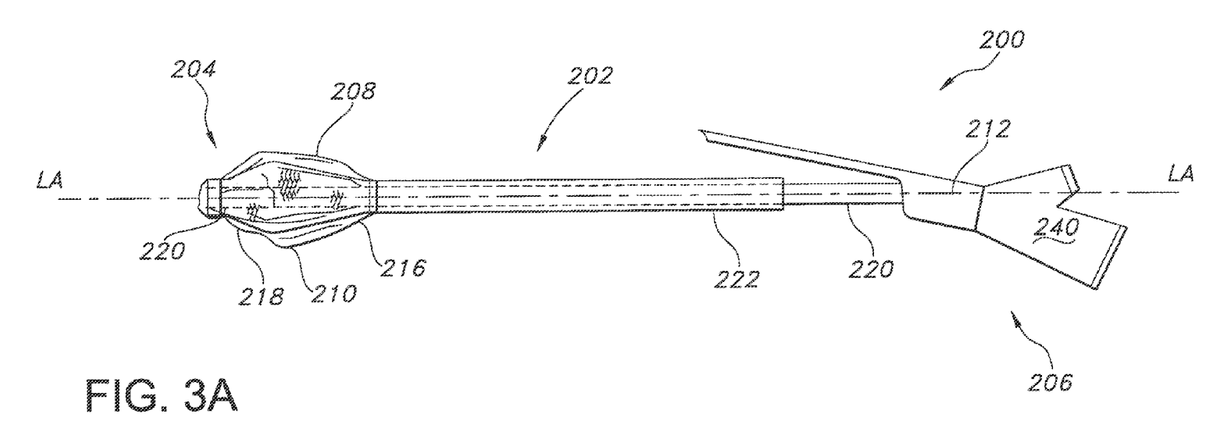
FIG. 3A is a side view illustrating an exemplary configurable PEG (or C-PEG) in an "insertion/removal" state.
Figure 3B:
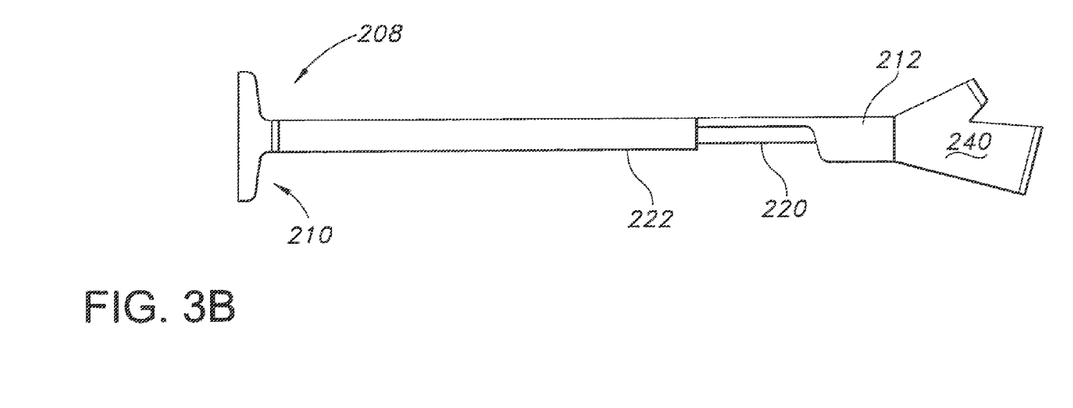
FIG. 3B is a side view illustrating an exemplary configurable PEG (or C-PEG) in a "deployed" state.

Turning now to FIG. 3 of the drawings, there is shown at 200 a configurable PEG device (also referred to as a "C-PEG" or "C-PEG device"). The device 200 includes a flexible shaft 202 (which may also be referred to as a "feeding tube" or "catheter") having a first or distal end 204 that is in-dwelling and a second or proximal end 206 that resides outside the body of a patient and a longitudinal axis "LA" extending from the first end 204 to the second end 206. The shaft 202 defines a lumen (not illustrated) for passage of feeding solutions and/or medicine. The shaft 202 includes an expandable retainer 208 at the first end 204 of the shaft 202, the retainer 208 having a deployed position and an insertion position. The C-PEG also includes a flexible sheath 210 surrounding the expandable retainer 208, the sheath 210 being generally loose around the retainer 208 when the retainer is in an insertion position and the sheath being generally snug against an exterior surface of the retainer when the retainer is in a deployed position.

The CPEG device 200 incorporates a releasable lock 212 for maintaining the expandable retainer in its deployed position. As used herein, the term "lock" refers to an element that secures two or more components in position relative to each other by engagement or interlocking of parts, friction, compression or other techniques and may encompass individual or integrated mechanisms such as clamps, detents, clips, magnets, intermeshing threaded components, fasteners (e.g., mechanical hook & loop fastening systems), refastening/reusable adhesives or the like. The releasable lock 212 is located at or near the second end 206 of the shaft 202. Generally speaking, the C-PEG device 200 also includes a base 240 which has an opening (not shown) allowing access through the base. The shaft 202 is desirably positioned through the base 240 in communication with the opening in the base. As noted above, the shaft 202 has walls defining a lumen from the opening in the base to the distal end of the shaft. The base 240 is generally located proximal to the releasable lock 212. It is contemplated that the releasable lock 212 may be integrated in the base 240.

Figure 4:
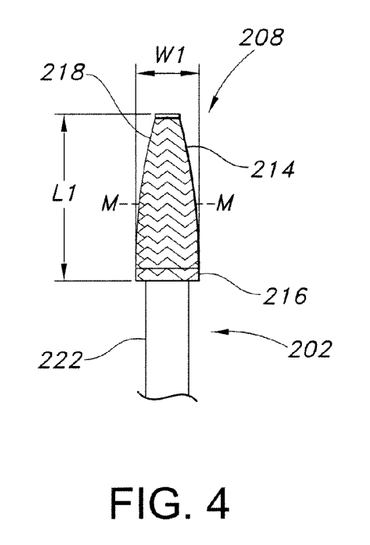
FIG. 4 is a side view illustrating a detail of an expandable retainer of an exemplary configurable PEG (or C-PEG) in an "insertion/removal" state.
Figure 5A:
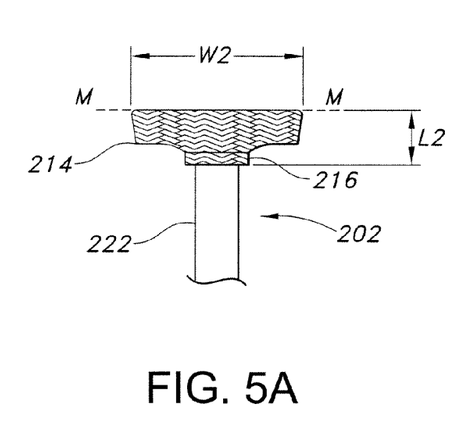
FIG. 5A is a side view illustrating a detail of an expandable retainer of an exemplary configurable PEG (or C-PEG) in a deployed state.
Figure 10:
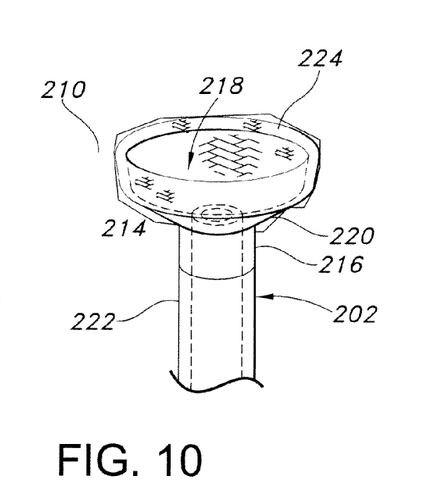
FIG. 10 is a side view illustrating a detail of an expandable retainer and flexible sheath of an exemplary configurable PEG (or C-PEG) in a deployed state.

Referring now to FIGS. 4 and 5A of the drawings, the expandable retainer 208 alternates between: (a) an insertion/removal state illustrated in FIG. 4 in which the expandable retainer 208 has a first length "L1" such that struts and/or other elements 214 of the retainer 208 are substantially axially aligned with the exterior of the shaft 202 such that the retainer 208 has a first width "W1" that is substantially the same as that of the shaft 202 to provide a cross-sectional area (i.e., in a plane that is perpendicular to the longitudinal axis "LA" of the CPEG device 200) that is also substantially the same as that of the shaft 202, and (b) a deployed state in which the retainer 208 has a second length "L2" that is shorter than the first length "L1" in which the struts and/or other elements 214 of the retainer are reconfigured such that the retainer 208 has a second width "W2" that is substantially greater than the first width "W1" to provide an effective cross-sectional area with a diameter that is substantially greater than that of the shaft 202. As can be seen in FIG. 4, the expandable retainer 208 has a midpoint "M" along it length L1 located between the opposing ends 216 and 218 of the retainer (i.e., the first end 216 and the second end 218 of the retainer 208 which correspond to the proximal end 216 and distal end 218 of the retainer in the un-deployed or insertion state). During deployment of the expandable retainer, the second end 218 of the retainer is drawn past the midpoint M towards the first end 216 to arrive at the deployed position as shown in FIGS. 5A and 10.

The expandable retainer 208 is generally in the form of a hollow sleeve or flexible skeleton that has two opposing ends 216 and 218. This sleeve is desirably formed of a flexible plastic mesh, braided material, braided mesh-like materials (e.g., braid of monofilament fibers), net or network of material, and/or flexible ribs (e.g., desirably flat ribs) composed of one or more materials such as, for example, PET (polyethylene terephthatlate), PEEK (poly(ether-ether-ketone)), or nylon (various polyamides).

Figure 5B:
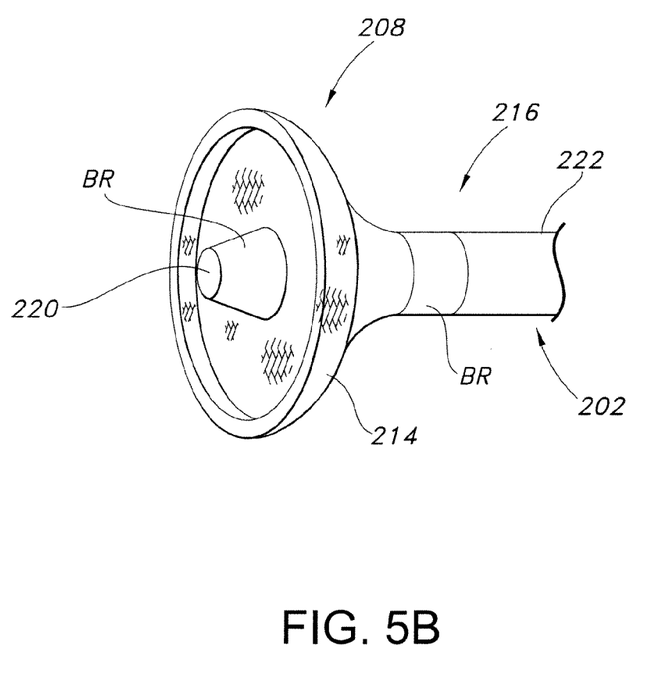
FIG. 5B is a side perspective view illustrating a detail of an expandable retainer of an exemplary configurable PEG (or C-PEG) in a deployed state.

In an aspect of the invention and referring now to FIG. 5B of the drawings, the first end 216 and/or the second end 218 of the expandable retainer 208 may be fused, joined or consolidated together to form a generally integrated area or ring which may be referred to as a "bonding ring" labeled as "BR". Generally speaking, the bonding ring BR is formed by fusing or consolidating portions of the expandable retainer 208 using heat, compression and/or solvent welding (which may be carried out on a mandrel or similar device) such that the relevant portions form an annular surface to join the ends of the retainer to the respective inner and outer tubes, reduce the overall profile or thickness of the connection (particularly where the first end 216 of the retainer 208 is joined to the outer tube 222) which eases insertion and removal, and/or reduce the likelihood of irritation or complication caused by fraying of the expandable retainer (e.g., secures monofilament fibers together so they do not project and cause irritation). The thickness of the bonding ring BR may be varied to provide a taper and/or may be molded to have a shape or configuration that fits or engages with a counterpart profile on an inner tube and/or outer tube.

The bonding ring BR is particularly useful for aiding the smooth transition of flexible plastic mesh, braided materials, braided mesh-like materials (e.g. braid of monofilament fibers), nets or network of materials with the surface of the outer tube 222 to provide a very smooth, low profile interface. This very smooth, low profile interface between the mesh 214 of the retainer 208 and the outer tube 222 reduces irritation and also reduces friction during insertion and/or removal of the C-PEG device 200 through a stoma. The bonding ring BR may be configured to act as a "stop" when the end 218 of the retainer is drawn past the midpoint M towards the end 216 to arrive at the deployed position. That is, a portion of the bonding ring at the end 216 may be shaped or flared to provide a flange, lip or rim such that it serves as a check or stop that controls the amount of retraction of the first or inner tube 220 into the second or outer tube 222 or prevents the end 218 from retracting completely into the second or outer tube 222. Alternatively and/or additionally, a protrusion, knob, annular ring, flange or the like may be formed at an appropriate location on the first or inner tube 220 to serve as a check or stop to control the amount of retraction of the first or inner tube 220 into the second or outer tube 222 or to prevent the end 218 from retracting completely into the second or outer tube 222.

As is illustrated in FIGS. 5A, 5B and 10, the axial movement that inverts the flexible (e.g., mesh) material of the retainer sleeve onto itself creates a resilient retention bumper at least by the presence of the double layer of material. This double layer helps reinforce the deployed retainer. As is also evident from FIGS. 5A, 5B and 10, the axial movement inverts portions of the mesh or braided material or other flexible material of the retainer onto itself to generate a flatter proximal profile that provides greater stabilization than rounded or funneled proximal profiles found in conventional retainers. This profile may be enhanced by thermally molding the flexible material to impart the flatter profile. In an aspect of the invention, the deployed retainer may define at least one generally planar surface and at least one generally frustoconical surface and/or cylindrical surface. For example, one or more generally planar surfaces may be generally perpendicular to the longitudinal axis of the shaft and one or more generally frustoconical surface and/or cylindrical surface may be generally parallel to the longitudinal axis of the shaft.

Figure 6:
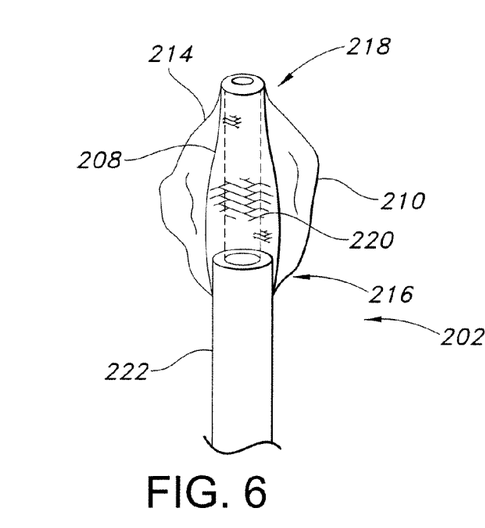
FIG. 6 is a side view illustrating a detail of an expandable retainer and flexible sheath of an exemplary configurable PEG (or C-PEG) in an "insertion/removal" state.

Referring to FIG. 6, all or substantially all the exterior surface of the retainer 208 is covered in a flexible sheath 210 that allows unencumbered changes in retainer shapes and states as desired. The flexible sheath avoids in-growth of tissue, is desirably (but not necessarily) non-permeable to liquid, and is generally non-compliant (i.e., the flexible sheath is generally not stretchable like an elastic material). This flexible sheath 210 may be attached at or towards each opposing end 216 and 218 of the retainer 208 to envelop at least a substantial portion of the retainer but not to embed within it. For example, the flexible sheath 210 may be attached to the retainer 208 at the bonding rings BR. In that regard, the bonding rings BR provide a satisfactory surface for attachment of the flexible sheath. Alternatively and/or additionally, the flexible sheath 210 may be joined to the inner tube 220 and/or the outer tube 222.

Figure 7:
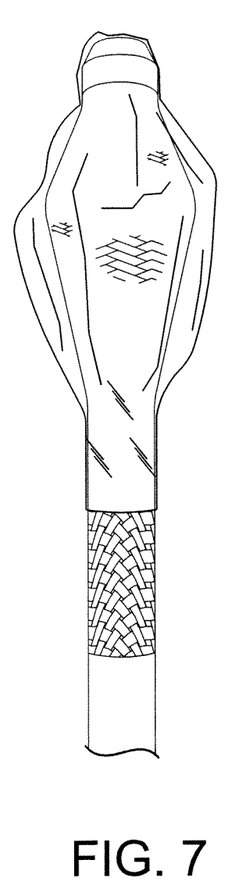
FIG. 7 is a side view photograph illustrating a detail of an expandable retainer and flexible sheath of an exemplary configurable PEG (or C-PEG) in an "insertion/removal" state.
Figure 8:
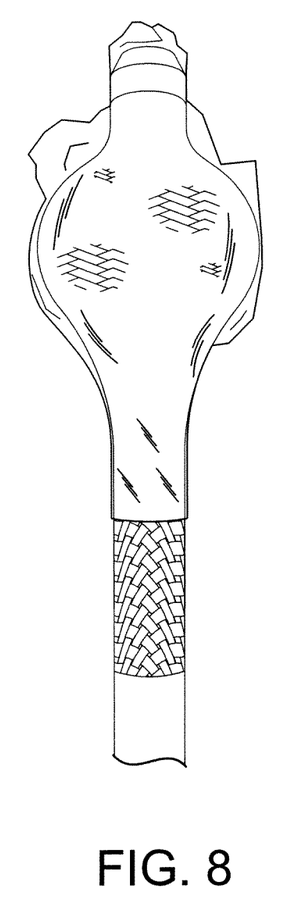
FIG. 8 is a side view photograph illustrating a detail of an expandable retainer and flexible sheath of an exemplary configurable PEG (or C-PEG) in a partially deployed state.
Figure 9:
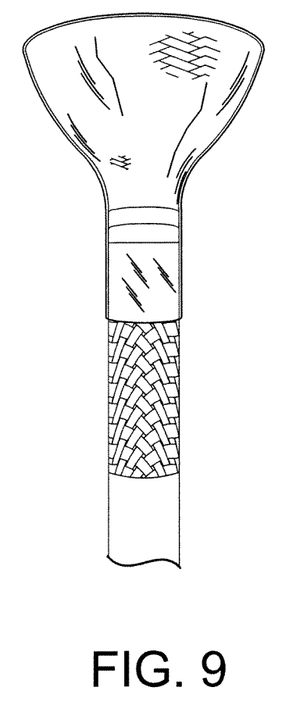
FIG. 9 is a side view photograph illustrating a detail of an expandable retainer and flexible sheath of an exemplary configurable PEG (or C-PEG) in a deployed state.

The flexible sheath 210 may snugly conform to the retainer in the deployed state as illustrated in the sequence of FIGS. 7 to 9. FIG. 7 is a photograph showing the sheath 210 in a loose condition around the expandable retainer 208. FIG. 8 is a photograph showing the sheath 210 enveloping the expandable retainer 208 as the retainer is being deployed. The sheath 210 allows the expandable retainer 208 to expand within it. FIG. 9 is a photograph of the sheath 210 fitting snugly around the deployed retainer 208. As used herein with respect to the conformance of the sheath 210 around the deployed retainer 208, the terms "snugly" and "generally snugly" should be understood that the fit or conformance of the sheath should avoid being so tight as to generate forces that distort the deployed retainer 208 into an undesirably frustum or frustoconical shape. That is, the sheath 210 should be close fitting but not tight, constricting, drawn out or stretched. The sheath prevents liquid from passing from the exterior of the retainer through the retainer when the sheath and retainer are properly assembled as part of the C-PEG. It is contemplated that the flexible sheath 210 may be formed from various materials including, but not limited to, polyurethane (PU), polyethylene (PE), polyvinyl chloride (PVC), polyamide (PA), or polyethylene teraphthalate (PETP). Additionally, copolymer admixtures for modifying the characteristics of the material may be used, for example a low density polyethylene and ethylene-vinyl acetate copolymer (LDPE-EVA), or blends of the above mentioned materials (e.g. PU with PVC or PU with PA) would be considered suitable for forming the flexible sheath. An exemplary material is a thermoplastic polyurethane elastomeric material identified as Pellethane® which is available from Lubrizol Advanced Materials, Inc.—Thermedics™ Polymer Products, Wilmington, Mass. A particularly useful thermoplastic polyurethane material is Pellethane® 2363-90A TPU. The thickness of the flexible sheath may be on the order of about 5 to about 100 micrometers as measured in the central region of the sheath. This thickness may be determined by conventional techniques utilizing a digital contact device such as, for example a Mitutoyo Litematic Digimatic Measuring Unit in accordance with the appropriate use procedures.

Referring to FIGS. 3 and 6, the shaft 202 has at least a first tube 220 and a second tube 222 that are arranged to form at least one effective lumen that spans the entire length of the shaft 202 (i.e., essentially the entire length of the C-PEG). The first tube 220 is desirably concentric within or surrounded by the second tube 222. That is, the first tube 220 is generally an inner tube and the second tube 222 is an outer tube. The first and second tubes are configured to axially slide with respect to each other. Generally speaking, the first tube 220 is longer than the second tube 222. The first tube 220 and the second tube 222 have respective distal and proximal ends that correspond to the orientation of the distal end 204 and proximal end 206 of the shaft 202. In an aspect of the invention, the overall length of the C-PEG is not significantly altered when the retainer alternates between the insertion and deployed states.

Generally speaking, a second end 218 of the retainer 208 is joined to the distal portion or end of the first or inner tube 220 and a first end 216 of the retainer 208 is joined to a distal portion or end of the second or outer tube 222. When the retainer 208 is in an insertion position (or in an un-deployed state), the first or inner tube 220 generally extends a distance beyond the end of the second or outer tube 222 as generally illustrated in FIG. 6 such that the second end 218 of the retainer 208 is extended axially and the rest of the retainer 208 is pulled inwardly against the first and second tubes such that the retainer assumes a tubular configuration.

Referring now to FIG. 10, there is shown an illustration of a portion of an exemplary C-PEG device 200 highlighting the retainer 208 in a deployed position. In such deployed position, the retainer 208 is configured to have a hemispherical-, dome- or mushroom-type shape. Such a shape is generated by retracting the first or inner tube back 220 into the second or outer tube 222. The expandable retainer 208 has a midpoint "M" along it length L1 located between the opposing ends 216 and 218 of the retainer (i.e., the first end 216 and the second end 218 of the retainer 208 which correspond to the proximal end 216 and distal end 218 of the retainer in the un-deployed or insertion state). During deployment of the expandable retainer, the second end 218 of the retainer is drawn past the midpoint M towards the first end 216 to arrive at the deployed position. This axial movement inverts portions of the mesh material 214 of the retainer 208 onto itself to create a resilient retention bumper. In an aspect of the invention, this axial movement inverts part of the mesh material 214 onto itself creating a flatter proximal profile that provides greater stabilization than the rounded or funneled proximal profiles found in conventional retainers. In its deployed state, the end 218 of the retainer can be drawn far enough past the midpoint M towards the end 216 to arrive at the deployed position such that the retainer 208 has a fold-over edge 224 formed by the mesh 214 (i.e., the area where the mesh folds back or inverts on itself) that is drawn inwardly toward a center point or central axis of the shaft such that the problem of tissue growing over the top of the deployed retainer is reduced.

Figure 11:
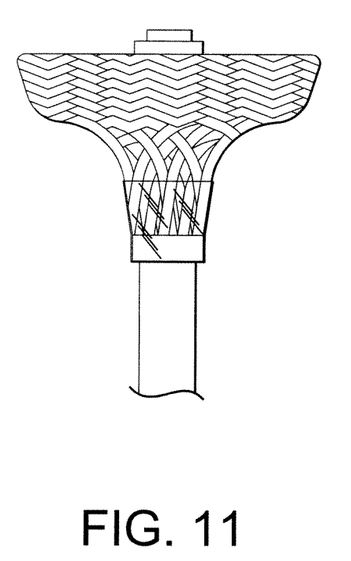
FIG. 11 is a side view photograph illustrating a detail of an expandable retainer of an exemplary configurable PEG (or C-PEG) in a deployed state.
Figure 12:
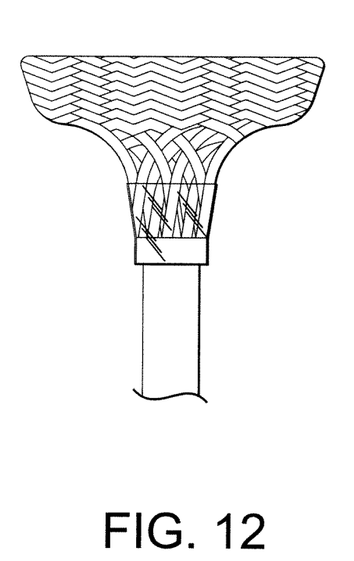
FIG. 12 is a side view photograph illustrating a detail of an expandable retainer of an exemplary configurable PEG (or C-PEG) in a deployed state.

Another feature of the C-PEG is the ability for the distal end of the shaft to recess within the deployed retainer as generally illustrated in FIG. 10 and in the photographs of FIGS. 9 and 12. FIG. 11 is a photograph illustrating an incomplete recess of the distal end of the shaft. FIG. 12 illustrates a more complete recess, that is, during deployment of the retainer, the distal end of the first or inner tube 220 is located in a more proximal position than the fold-over edge 224 of the deployed retainer 208. This prevents the first or distal end 204 of the shaft 202 (i.e. the distal end of the first or inner tube 220) from contacting tissue when the retainer 208 is in the deployed state.

Figure 13:
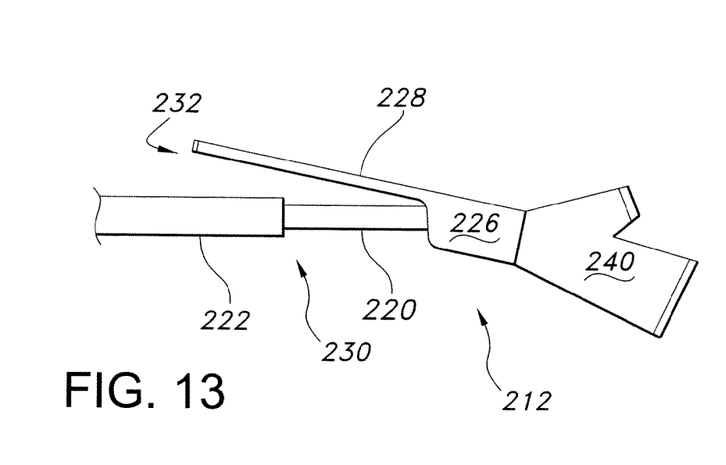
FIG. 13 is a side view illustrating a detail of a releasable lock of an exemplary configurable PEG (or C-PEG).

According to the invention, the releasable lock 212 locks the expandable retainer 208 in its deployed state. One embodiment of a suitable releasable lock 212 is a spacer lock. FIG. 13 is a side view illustration of a spacer lock composed of a fitting 226 that securely connects the lock 212 to the first tube 220 and a movable latch arm 228 having an end 232. The fitting 226 and latch arm 228 may be part of the base 240, either molded with the head as a unitary component or over molded to reduce the number and expense of parts to a minimum. Alternatively, the fitting 226 and latch arm 228 may be independent components; when independent, substitute components with slightly different dimensions can be used to provide different pre-determined separation distances. The first or inner tube 220 is shown attached to the base 240 and passing into and through the outer tube 222.

Figure 14:
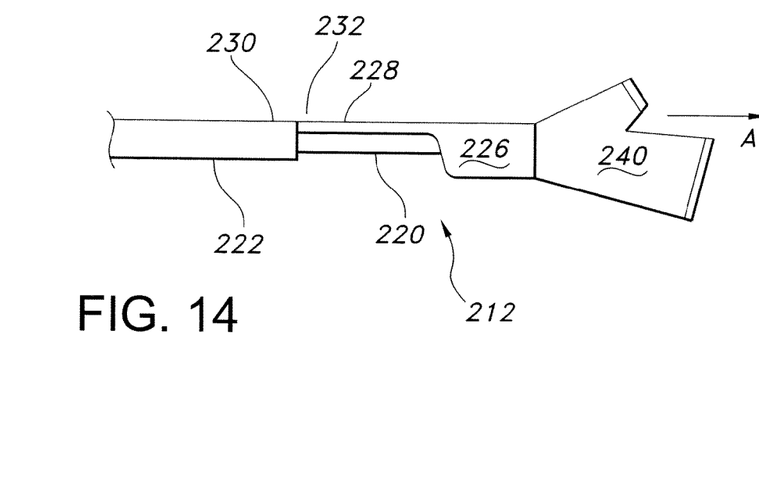
FIG. 14 is a side view illustrating a detail of a releasable lock of an exemplary configurable PEG (or C-PEG).
Figure 15:
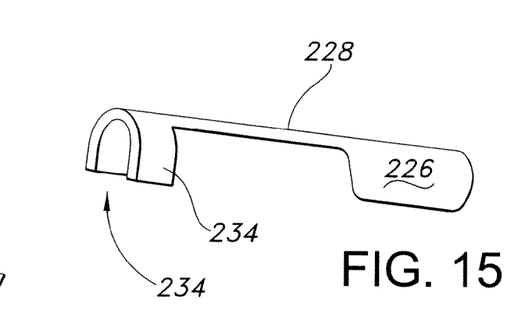
FIG. 15 is a side view illustrating a detail of a releasable lock of an exemplary configurable PEG (or C-PEG).

Referring to FIG. 14, when the inner tube 220 is pulled or retracted through the second or outer tube 222 towards the proximal end of the shaft to deploy the retainer (and/or the outer tube 222 is pushed away from the base 240 toward the distal end 204 of the shaft), the proximal end of the first tube 220 will move in the direction of the arrow "A" to extend a predetermined separation distance beyond the proximal end of the second tube 222. A spacer in the form of the movable latch arm 228 may be employed such that the end 232 of the latch arm 228 swings into place to rest against a face 230 of the second tube 222 (or other feature such as, for example, a projection or lip) to prevent the second (i.e., outer) tube 222 from returning to its initial insertion or un-deployed position and to keep the predetermined separation distance fixed. An exemplary separation distance may be about one (1) inch (~25 mm).

The end 232 of the latch arm 228 may have opposing clamp-like extensions 234 (e.g., parts that partially encircle the inner tube 220) that are stiff enough so that they remain around the inner tube 220 despite forces normal to the inner tube 220. The clamp-like extensions 234 are configured to fit or wrap around the first tube 220 so that the outer tube 222 butts up against them. The majority of the force that resists the outer tube 222 from returning to its original position is taken up by the latch arm 228 connecting the clamp-like extensions 234 to the fitting 226 and/or the base 240. Other embodiments of the spacer lock do not require clamp-like extensions to be wrapped around the first inner tube but may utilize an element or feature that just wraps around the first inner tube to keep the latch arm 228 in place.

Figure 16:
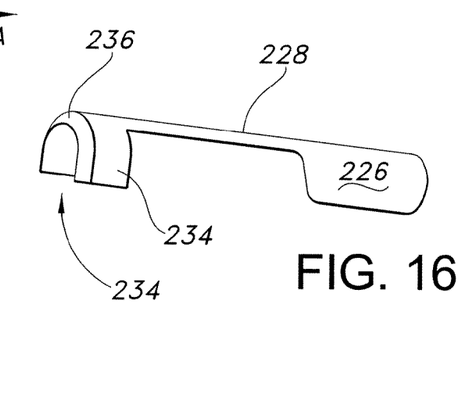
FIG. 16 is a side view illustrating a detail of a releasable lock of an exemplary configurable PEG (or C-PEG).

In an embodiment, the clamp-like extensions 234 or the end 232 of the latch arm 228 can be configured to create friction between the inner tube 220 and the outer tube 222 that keeps the expandable retainer 208 in its deployed state. Referring to FIG. 16, there is illustrated an optional lip 236 that may be included on the end of the latch arm 228. The lip 236 may be at the end of the opposing clamp-like extensions 234 as shown in FIG. 16 or the lip may be provided at the end 232 of the latch arm 228. The lip 236 is desirably tapered so it can effectively wedge in between the inner tube 220 and outer tube 222. The lip 236 seats between the inner tube 220 and outer tube 222 to provide a frictional fit that locks the two tubes in position. To unlock, the inner tube 220 is axially pulled out so that the lip 236 unseats from between the inner and outer tubes and allows the latch arm 228 to swing away from the inner tube 220.

The end of the latch arm 228 closest to the base should be flexible to allow swing positioning. The portions of the releasable lock 212 that form the clamp-like extensions 234 desirably have a relatively higher level of stiffness to keep the latch arm 228 in place. These clamp-like extensions 234 should be stiff enough to avoid becoming unintentionally opened and must be rigid enough to withstand normal wear and tear. The other portions of the releasable lock 212 need to be flexible enough to withstand repeated use by locking and unlocking; they can also be made to compensate for minor changes in the stoma tract. It is contemplated that other integrated locking mechanism such as clamps, detents, clips, magnets, fasteners or the like can also be used.

Figure 17:
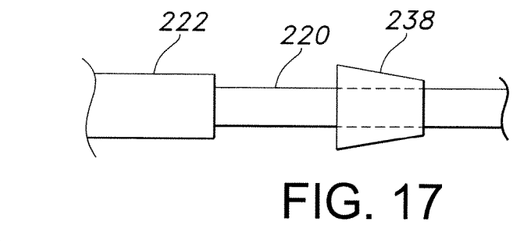
FIG. 17 is a side view illustrating a detail of a releasable lock of an exemplary configurable PEG (or C-PEG).
Figure 19:
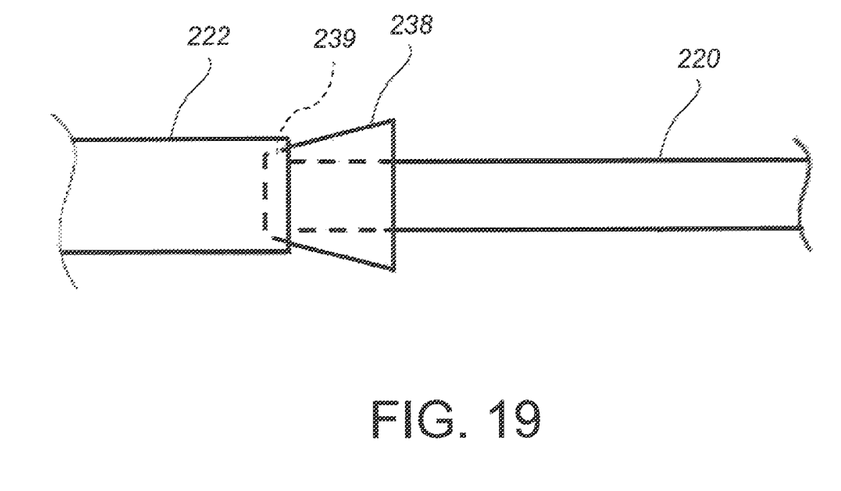
FIG. 19 is a side view illustrating a detail of a releasable lock of an exemplary configurable PEG (or C-PEG).

In another embodiment illustrated in FIG. 17, the releasable lock 212 does not utilize a spacer lock with a latch arm 228 but instead uses an annular clamp or ring 238 that is securable to the inner tube 220. After the expandable retainer 208 is deployed, the clamp 238 is secured to inner tube 220 and clamped down with enough force to ensure the clamp 238 cannot slide or be displaced axially along the length of the inner tube 220 but not too much force as to deform the lumen that is defined by the walls of the inner tube 220. In one form, the clamp 238 may secured to the inner tube 220 so that the second tube 222 butts up against it and the clamp prevents the second tube 222 from returning to a position in which the expandable retainer is in an un-deployed or insertion state. In another form, the clamp 238 may include a lip 239 (FIG. 19) which is desirably tapered so it can effectively wedge in between the inner tube 220 and outer tube 222. When such clamp 238 is secured to the inner tube 220, the lip seats between the inner tube 220 and outer tube 222 to provide a frictional fit that locks the two tubes in position thereby preventing the second tube 222 from returning to a position in which the expandable retainer is in an undeployed or insertion state.

Figure 18:
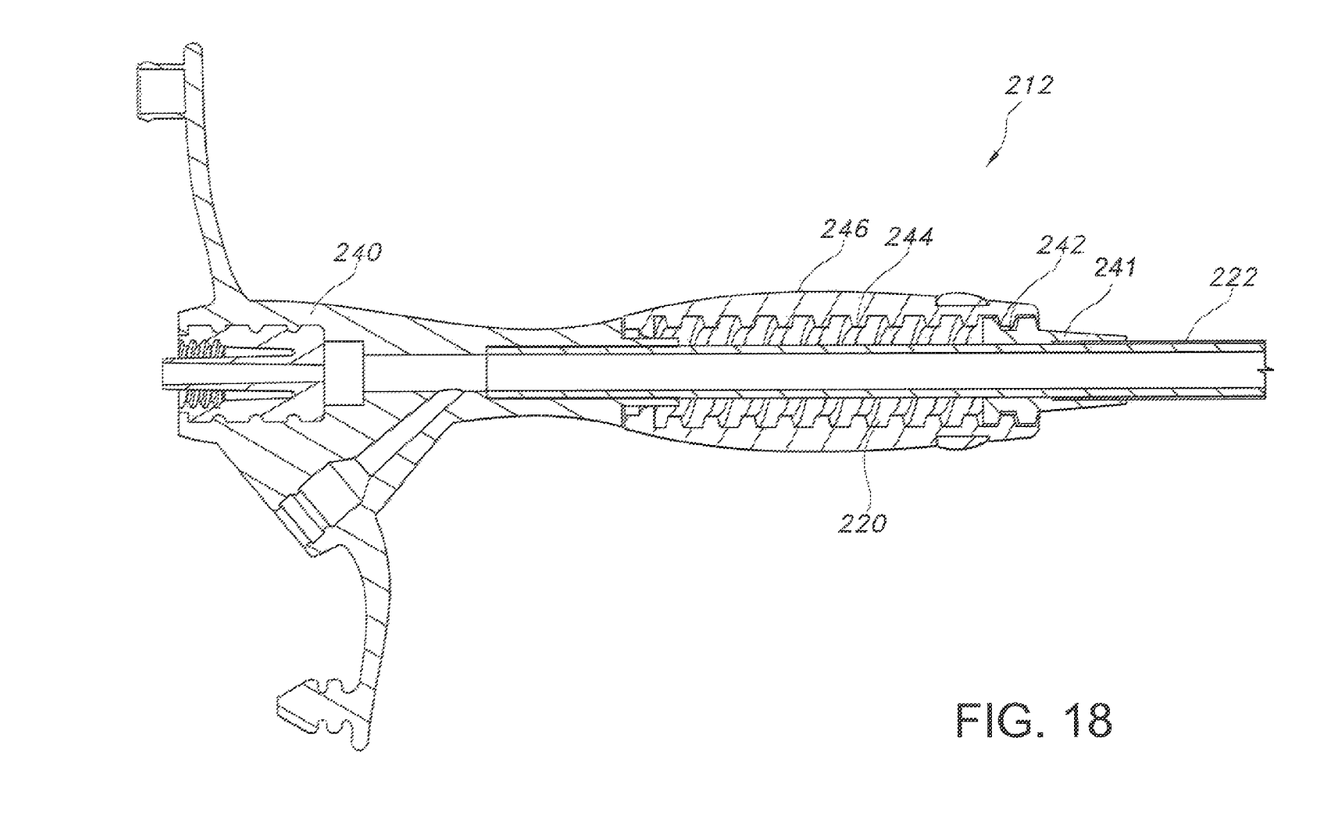
FIG. 18 is a side cross-sectional view illustrating a detail of a releasable lock of an exemplary configurable PEG (or C-PEG).

In yet another embodiment illustrated in FIG. 18, the releasable lock 212 utilizes an annular ring 241 that is secured to the outer tube 222. The ring 241 includes a recess 242 to receive threads 244 defined in a cover 246 in rotational communication with the inner tube 220 In order to deploy the expandable retainer 208, the cover 246 is rotated so the threads 244 engage the recess in the annular ring 241 to move the cover 246 and the inner tube 220 in the desired direction. A decent or lock may be used to secure the cover from further rotation after the inner tube 220 is in position and the expandable retainer 208 is deployed. Alternatively, the cover 246 may be configured to rotate in a stationary position on the outer tube 222 and an annular ring secured to the inner tube 220 may have a recess that engages the threads 244 on the cover such that rotating the cover causes the annular ring and the inner tube 220 to advance in the desired direction. Other configurations employing threaded components, detents, snaps or clips are contemplated.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. A configurable percutaneous endoscopic gastrostomy tube comprising:
    a shaft having a distal end and a proximal end, the shaft defining a lumen therethrough for passage of a feeding solution or medicine, the shaft further comprising an outer tube and an inner tube slidably positioned in the outer tube, the inner tube movable within the outer tube, the outer tube having a distal end and a proximal end;
    an expandable retainer secured to the shaft, the expandable retainer having a deployed position and an insertion position, the expandable retainer defining a first end, a second end, and a midpoint, the second end movable with respect to the first end;
    a releasable lock for maintaining the expandable retainer in its deployed position, the releasable lock comprising an annular clamp securable to the inner tube of the shaft proximal to the expandable retainer, wherein when the annular clamp is secured to the inner tube, the annular clamp encircles the inner tube and the proximal end of the outer tube butts up against the annular clamp to prevent the outer tube from returning to a position in which the expandable retainer is in the insertion position; and
    a flexible sheath surrounding the expandable retainer, the sheath being generally loose around the retainer when the retainer is in the insertion position and the sheath being generally snug against an exterior surface of the retainer when the retainer is in the deployed position,
    wherein the expandable retainer is a flexible material that folds back on itself to form a double layer of material when the second end is drawn past the midpoint toward the first end.

2. The configurable percutaneous endoscopic gastrostomy tube of claim 1, wherein the annular clamp includes a lip that is tapered, wherein the lip is configured to wedge in between the inner tube and the outer tube to provide a frictional fit that locks the inner tube and the outer tube in position.

3. The configurable percutaneous endoscopic gastrostomy tube of claim 1, wherein the first end of the expandable retainer is joined with the outer tube and the second end of the expandable retainer is joined with the inner tube.

4. The configurable percutaneous endoscopic gastrostomy tube of claim 3, wherein the flexible sheath has a first end and a second end, the first end being joined with the outer tube and the second end joined with the inner tube.

5. The configurable percutaneous endoscopic gastrostomy tube of claim 1, wherein the expandable retainer, when in its insertion position, generally conforms to an axial configuration of the shaft and the deployed position of the expandable retainer is obtained by drawing the second end of the retainer past the midpoint to the first end of the retainer.

6. The configurable percutaneous endoscopic gastrostomy tube of claim 1, wherein the second end of the expandable retainer is drawn past the midpoint to the first end so that the first end of the shaft is recessed in the expandable retainer.

7. The configurable percutaneous endoscopic gastrostomy tube of claim 1, wherein the flexible material is formed of a net, mesh or braided structure.

8. The configurable percutaneous endoscopic gastrostomy tube of claim 1, wherein the flexible material is fused or consolidated to provide bonding rings at least at one end of the expandable retainer.

9. The configurable percutaneous endoscopic gastrostomy tube of claim 1, wherein the expandable retainer is located at the distal end of the shaft.

10. The configurable percutaneous endoscopic gastrostomy tube of claim 1, wherein the releasable lock is located at or near the proximal end of the shaft.

11. The configurable percutaneous endoscopic gastrostomy tube of claim 1, wherein the double layer of material of the expandable retainer forms a resilient retention bumper.

12. The configurable percutaneous endoscopic gastrostomy tube of claim 1, wherein the double layer of material of the expandable retainer defines a fold-over edge where the material inverts on itself.

13. The configurable percutaneous endoscopic gastrostomy tube of claim 1, wherein the expandable retainer in the deployed position defines at least one generally planar surface and at least one generally frustoconical surface.

14. The configurable percutaneous endoscopic gastrostomy tube of claim 1, wherein the expandable retainer in the deployed position defines at least one generally planar surface and at least one generally cylindrical surface.

\* \* \* \* \*